US012565175B2

(12) United States Patent
Hök et al.

(10) Patent No.: US 12,565,175 B2
(45) Date of Patent: Mar. 3, 2026

(54) METHOD AND SYSTEM FOR DETERMINATION AND CLASSIFICATION OF INTOXICATING SUBSTANCE IN A BREATH SAMPLE FACILITATED BY A USER INTERACTION SCHEME

(71) Applicant: Automotive Coalition for Traffic Safety, Inc., Leesburg, VA (US)

(72) Inventors: Bertil Hök, Västerås (SE); Jonas Ljungblad, Stockholm (SE)

(73) Assignee: Automotive Coalition for Traffic Safety, Inc., Ashburn, VA (US)

( * ) Notice: Subject to any disclaimer, the term of this patent is extended or adjusted under 35 U.S.C. 154(b) by 391 days.

(21) Appl. No.: 18/018,375

(22) PCT Filed: Jul. 8, 2021

(86) PCT No.: PCT/SE2021/050698
§ 371 (c)(1),
(2) Date: Jan. 27, 2023

(87) PCT Pub. No.: WO2022/025811
PCT Pub. Date: Feb. 3, 2022

(65) Prior Publication Data
US 2023/0286466 A1     Sep. 14, 2023

(30) Foreign Application Priority Data

Jul. 29, 2020    (SE) .................................... 2050930-3

(51) Int. Cl.
| | |
|---|---|
| B60R 25/25 | (2013.01) |
| A61B 5/00 | (2006.01) |
| A61B 5/08 | (2006.01) |
| B60K 35/10 | (2024.01) |
| B60K 35/22 | (2024.01) |
| B60K 35/26 | (2024.01) |

(Continued)

(52) U.S. Cl.
CPC ............ B60R 25/257 (2013.01); A61B 5/082 (2013.01); A61B 5/4845 (2013.01); B60K 35/10 (2024.01);
(Continued)

(58) Field of Classification Search
None
See application file for complete search history.

(56) References Cited

U.S. PATENT DOCUMENTS

| | | | |
|---|---|---|---|
| 7,736,903 B2 | 6/2010 | Lambert et al. | |
| 7,919,754 B2 | 4/2011 | Hök et al. | |

(Continued)

FOREIGN PATENT DOCUMENTS

| | | |
|---|---|---|
| CN | 107195200 | 9/2017 |
| CN | 108074374 | 5/2018 |

(Continued)

*Primary Examiner* — Jay B Shah
(74) *Attorney, Agent, or Firm* — Pandiscio & Pandiscio

(57) ABSTRACT

The present invention relates to a breath analyzing system and method. In particular the invention relates to a breath analyzing system and method arranged to provide tracer-aided determination and classification of the presence of a breath intoxicating substance facilitated by a user interaction scheme. If a determination may not be performed within a first compliant mode of operation an interactive mode is initiated wherein the user is stepwise instructed to perform actions that facilitate the classification. An action compliance value, representing how well the user follows issued actions/instructions, is determined and used to select actions.

15 Claims, 4 Drawing Sheets

(51) Int. Cl.

| | | |
|---|---|---|
| *B60K 35/28* | (2024.01) | |
| *B60K 35/29* | (2024.01) | |
| *B60R 25/30* | (2013.01) | |
| *B60R 25/31* | (2013.01) | |
| *G01N 33/497* | (2006.01) | |

(52) U.S. Cl.

CPC .............. *B60K 35/22* (2024.01); *B60K 35/26* (2024.01); *B60K 35/28* (2024.01); *B60K 35/29* (2024.01); *B60R 25/305* (2013.01); *B60R 25/31* (2013.01); *G01N 33/4972* (2013.01)

(56) References Cited

U.S. PATENT DOCUMENTS

| | | | |
|---|---|---|---|
| 8,377,705 B2 | 2/2013 | Lambert et al. | |
| 9,746,454 B2 | 8/2017 | Hök et al. | |
| 2002/0084130 A1 | 7/2002 | Der Ghazarian et al. | |
| 2010/0268425 A1 | 10/2010 | Pettersson et al. | |
| 2017/0096146 A1* | 4/2017 | Jones .................... | B60W 40/08 |
| 2020/0101982 A1 | 4/2020 | Bowers et al. | |
| 2020/0122741 A1 | 4/2020 | Kuehnle et al. | |
| 2020/0215912 A1 | 7/2020 | DeVries et al. | |

FOREIGN PATENT DOCUMENTS

| | | | |
|---|---|---|---|
| EP | 1688741 | 8/2006 | |
| EP | 1688741 A2 * | 8/2006 | ............ B60K 28/06 |
| JP | 2008-191871 | 8/2008 | |
| JP | 2009-090866 | 4/2009 | |
| JP | 5240677 | 7/2013 | |
| JP | 2014-002162 | 1/2014 | |
| JP | 2020-004334 | 1/2020 | |
| SE | 2050105-2 | 3/2021 | |
| WO | WO 94/22686 | 10/1994 | |

* cited by examiner

METHOD AND SYSTEM FOR DETERMINATION AND CLASSIFICATION OF INTOXICATING SUBSTANCE IN A BREATH SAMPLE FACILITATED BY A USER INTERACTION SCHEME

REFERENCE TO PENDING PRIOR PATENT APPLICATIONS

This patent application is a 371 national stage entry of pending prior International (PCT) Patent Application No. PCT/SE2021/050698, filed 8 Jul. 2021 by Senseair AB for METHOD AND SYSTEM FOR DETERMINATION AND CLASSIFICATION OF INTOXICATING SUBSTANCE IN A BREATH SAMPLE FACILITATED BY A USER INTER-ACTION SCHEME, which patent application, in turn, claims benefit of Swedish Patent Application No. SE 2050930-3, filed 29 Jul. 2020.

The two (2) above-identified patent applications are hereby incorporated herein by reference.

FIELD OF THE INVENTION

The present invention relates to a breath analyzing system and method. In particular the invention relates to a breath analyzing system and method arranged to provide tracer-aided determination and classification of the presence of a breath intoxicating substance facilitated by a user interaction scheme.

BACKGROUND OF THE INVENTION

Breath analyzing equipment is becoming increasingly common, not the least in vehicles as a measure to detect and prevent driving under the influence of intoxicating substances, in particular, ethyl alcohol (ethanol). The breath analyzing equipment may be a stand-alone, even handheld, unit that gives a measured value of the content of a substance or substances in the driver's breath. Alternatively, breath analyzing equipment may be part of a system wherein also including equipment for identifying the driver and/or immobilizing the vehicle. Such breath analyzing equipment is typically permanently mounted in the vehicle and may be an integral part of the dashboard, for example. Breath analyzing equipment may also be stationary systems used to control access to a work area, a vehicle fleet depot or the like.

To provide a breath analyzer that has appropriate sensitivity, is reliable and provides a reasonably fast analysis is far from trivial. This is especially true if the breath analyzing equipment should be able to detect a plurality of substances and not being disturbed by variation in moisture, $CO_2$ content etc. Breath analyzing equipment that fulfills these requirements are described in for example U.S. Pat. Nos. 7,919,754 and 9,746,454, hereby incorporated by reference.

The breath analyzing equipment may be part of a system also including equipment for identifying the driver and/or immobilizing the vehicle, so called "alcolocks". Such breath analyzing equipment is typically permanently mounted in the vehicle and may be an integral part of the dashboard, for example, and connected to the control system of the vehicle. Alcolocks are in widespread use in offender programs as a mandatory accessory for rehabilitation of car owners who have been convicted for drunk driving. In addition, similar systems and devices are being used in commercial vehicles like buses, taxis and trains. However, it appears that these systems will also be common in private vehicles in a near future, and possibly also mandatory in at least some countries and regions.

The up to the present day most common approach for vehicle mounted breath testing equipment is to use a mouthpiece to which, after a deep breath, the user should empty his or her airways. This approach is referred to as active detection. To ensure a correct determination the user should deliver a forced expiration at almost full vital capacity. This requires substantial time and effort, especially for persons with limited capacity. In addition the mouthpiece, or part of the mouthpiece, is often a disposable plastic item for hygienic reasons. This results in cumbersome handling and the use of vast amounts of disposable plastic items, which would be the case if alcolocks become mandatory, is questionable from an environmental viewpoint.

An alternative approach is referred to as contactless detection wherein no mouthpiece is utilized and the breath testing apparatus typically receives a mixture of the exhaled breath and the surrounding air and a detection of an intoxicating substance is determined from a breath sample taken during the expiration at normal breathing. The detection may be truly passive wherein no action is required of the user, for example taking place while a user performs the regular starting up routine of a vehicle. Alternatively, the user may be instructed to perform certain actions that are meant to facilitate the detection process, for example the user may be instructed to breath towards an air inlet or the like. One challenge with contactless detection, even if user is instructed to breathe in a certain direction or the like, is the low concentration of the substances to be detected and analyzed. An established method is to utilize tracer gases, typically carbon dioxide or water vapor, which are always present in the breath in highly predictable amounts, to both trigger the analysis of the target substance and to facilitate the determination of the target substance concentration value. However, it has proven difficult to get the contactless detection to function in a satisfactory manner in real life scenarios. Even if data indicating the presence or absence of an intoxicating substance, will eventually be correctly analyzed, the time needed for such classification is too long to be acceptable in a vehicle wherein the alcolock holds up the vehicle until approval is given, for example. Hence systems and methods that provides quicker and more reliable feedback to the user/driver is needed, in particular, measurement errors must be handled in an effective manner.

The co-pending application SE 2050105-2 by the same applicant as the present invention discloses a breath analyzing system and method arranged to provide rapid tracer-aided classification of the presence of a breath intoxicating substance above a limit concentration and providing status to a user about the progression of the classification. SE 2050105-2 is hereby incorporated by reference.

U.S. Pat. No. 7,736,903 discloses a system and a method for passive detection of alcohol using a first and second tracer, and a first and second time period for compensating for environmental variations. The response time for such systems is typically minutes which is considered far too slow for practical use, both in automotive and other applications.

U.S. Pat. No. 8,377,705 discloses adding another tracer, water vapor, and another detection mode, in which the ethanol and tracer signals are measured at a first and a second time distinct from the first time. There is, however, no mention of how to avoid or manage measurement errors and the response time appears to be an issue also in this system/method.

US 2020/101982 concerns a breath alcohol sensor/analyzer, a microphone/speech recognition unit, and a loudspeaker/speech synthesizer. The speech synthesizer generates questions to be orally answered by the subject, thereby producing air flow detectable by the breath analyzer. The result of the analysis decides the drivability of a vehicle. The problems related to ambiguous or invalid sensor data are not addressed. Such ambiguities may result from signal interference, out-of-range ambient conditions, technical errors, or a poorly cooperative subject. The latter cause is considered to be dominant.

Thus, there is still a need to improve the breath analyzing equipment in vehicles in order to get a widespread acceptance for the technique. Most important is to make the tests fast and reliable for the driver/user that is sober and complies to the instructions on how to perform the testing. Ideally, the testing should, for the sober and compliant driver/user, not add any manual operations or cause any time delay in the starting up of the vehicle.

SUMMARY OF THE INVENTION

The object of the invention is to provide a breath analyzing system and method of operation that overcomes the drawbacks of prior art passive detection systems.

This is achieved by the method as defined in claim 1, and the breath analysis system as defined in claim 13.

According to one aspect of the invention a method for operating a breath analysis system is provided to determine restriction levels for a user performing a specified task based on a concentration of an intoxicating substance in the exhaled breath of the user and an analysis of the behavior of the user. The method comprises a compliant mode of operation and an interactive mode of operation, the method utilizing a predetermined set of restriction levels and a predetermined set of actions.

The compliant mode comprises the steps of:

sampling signals representing the local concentration of an intoxicating substance, analyzing the sampling result and determining from the analyzed results if the breath concentration of an intoxicating substance of the user may be classified within required levels of accuracy and precision;

if classification is determined to be possible to perform:

determining intoxicating substance breath concentration, and comparing the intoxicating substance breath concentration with a set of predetermined concentration intervals to select a restriction level from a predetermined set of restriction levels, wherein each predetermined concentration interval corresponds to a predetermined restriction level.

If classification is determined to not be possible to perform the method enters into the interactive mode of operation, the interactive mode of operation comprising the steps of:

issuing a selected action to the user from a set of predetermined actions, the selection of an instruction based on a session history log and an action compliance value, wherein the session history log comprises information on the issued selected actions in the present interactive mode session and the corresponding result of the issued selected actions, and the action compliance value is a value determined from the result of the issued selected actions. The result of the issued selected actions may be an improved determination of the intoxicating substance breath concentration or an output from secondary sensors;

sampling signals representing the local concentration of an intoxicating substance and analyzing the sampling result and determining from the analyzed results if the breath concentration of an intoxicating substance of the user may be classified within required levels of accuracy and precision;

if classification is determined to be possible:

determining the intoxicating substance breath concentration, and comparing the intoxicating substance breath concentration with a set of predetermined concentration intervals to select a restriction level from a predetermined set of restriction levels, wherein each predetermined concentration interval corresponds to a predetermined restriction level; and if classification is determined to not be possible:

determining an action compliance value based on an analysis of how well the user has complied to the issued selected action;

updating the session history log, the session history log at least comprising information of which action of the set of predetermined actions that have been issued;

repeating the steps of the interactive mode until a restriction level is established. Alternatively, or in combination, the steps are repeated until a predetermined maximum time period is reached.

According to one embodiment of the method the set of restriction levels comprises a plurality of restriction levels representing increasing limitations to drivability of the vehicle. The set of restriction levels may comprise one or more of the restriction levels corresponding to settings of the vehicle: drive without restriction, drive with warning issued, limited drivability, and ignition locking.

According to one embodiment of the method the set of predetermined actions comprises at least one of the subsets of: attention actions, instructive actions, requests for action, and warning actions. An attention action may comprise activating a visual attraction element.

According to one embodiment of the method an interaction unit is used by the breath analysis system to communicate a selected action to the user.

According to one embodiment of the method the step of comprises a further step to be taken upon a selected action being issued, the further step comprising receiving a confirmation from the user confirming comprehension and acceptance of the selected action.

According to one embodiment of the method the action compliance value is based on an analysis if the measurement of the intoxicating substance has improved the possibility to classify within required levels of accuracy and precision. Alternatively, or in combination the action compliance value determined is at least partly based on input provided by a secondary sensing unit.

According to one aspect of the invention the interactive mode of operation comprises the steps of:

issuing a selected action to the user from a set of predetermined actions, the selection of an instruction based on a session history log and an action compliance value, wherein the selected action is issued via the visual attraction element and/or the interaction unit;

sampling signals from a breath measurement unit representing the local concentration of an intoxicating substance and analyzing the sampling result, analyzing the sampling result and determining from the analyzed results if the breath concentration of an intoxicating substance of the user may be classified within required levels of accuracy and precision;

if classification is determined to be possible to perform with the required levels of accuracy and precision:

determining the intoxicating substance breath concentration, and comparing the intoxicating substance breath concentration with a set of predetermined concentration intervals to select a restriction level from a predetermined set of restriction levels, wherein each predetermined concentration interval corresponds to a predetermined restriction level; and if classification is determined to not be possible:

determining an action compliance value based on an analysis of how well the user has complied to the issued selected action, using input from at least one secondary sensing unit, the secondary sensing unit providing other information about the user than the breath measurement unit;

updating the session history log, the session history log comprising information of which action of the set of predetermined actions that have been issued;

repeating the steps of the interactive mode until a restriction level is established or a predetermined maximum time period is reached.

According to one embodiment of the method issuing the selected action comprises the breath analyzing system using one or a combination of the interaction units: a loudspeaker, and a display.

According to one embodiment of the method the determination of the action compliance value after the selected action is issued comprises using one or a combination of the secondary sensing units: a camera in combination with image analysis functionality, a microphone combined with voice recognition functionality, an IR sensor and seat occupation sensors.

According to one aspect of the invention a method a breath analysis system is provided. The breath analysis system comprises a breath measurement unit at least one visual attraction elements, at least one secondary sensing unit, at least one interaction unit, and a CPU. The breath analysis system is configured to provide a compliant mode comprising the steps of:

sampling signals from the breath measurement unit representing the local concentration of an intoxicating substance, analyzing the sampling result and determining from the analyzed results if the breath concentration of an intoxicating substance of the user may be classified within required levels of accuracy and precision;

if classification is determined to be possible to perform:

determining intoxicating substance breath concentration, and comparing the intoxicating substance breath concentration with a set of predetermined concentration intervals to select a restriction level from a predetermined set of restriction levels, wherein each predetermined concentration interval corresponds to a predetermined restriction level, and if classification is determined to not be possible to perform the provide an interactive mode of operation, the interactive mode of operation comprising the steps of:

issuing a selected action to the user from a set of predetermined actions, the selection of an instruction based on a session history log and an action compliance value, wherein the selected action is issued via the visual attraction element and/or the interaction unit;

sampling signals from a breath measurement unit representing the local concentration of an intoxicating substance and analyzing the sampling result, analyzing the sampling result and determining from the analyzed results if the breath concentration of an intoxicating substance of the user may be classified within required levels of accuracy and precision;

if classification is determined to be possible to perform with the required levels of accuracy and precision:

determining the intoxicating substance breath concentration, and comparing the intoxicating substance breath concentration with a set of predetermined concentration intervals to select a restriction level from a predetermined set of restriction levels, wherein each predetermined concentration interval corresponds to a predetermined restriction level; and if classification is determined to not be possible:

determining an action compliance value based on an analysis of how well the user has complied to the issued selected action, using input from at least one secondary sensing unit, the secondary sensing unit providing other information about the user than the breath measurement unit;

updating the session history log, the session history log comprising information of which action of the set of predetermined actions that have been issued;

repeating the steps of the interactive mode until a restriction level is established or a predetermined maximum time period is reached.

Thanks to the invention it is possible to provide a breath analysis method and system which significantly reduces the time to a reliable classification in the vast majority of testing situations. In particular the testing will be fast and convenient for the sober user who is compliant to given instructions.

One advantage afforded by the present invention is that the system utilizes much of equipment often already provided in a vehicle, for example a touch screen, a voice recognition system and various sensors/detectors.

Another advantage is that the method provides an extension of the actions that may be provided to a user, for example providing warnings to the user not necessarily above a legal limit for an intoxicating substance, but still calling for attention. The warnings may be given in a manner that also passengers in the vehicles are informed.

One further advantage is that the actions required from the user is stepwise increased in complexity, and thereby also in time needed to perform the action and/or analyze the result. Thereby complex and time-consuming actions are only utilized when actually needed.

In the following, the invention will be described in more detail, by way of example only, with regard to non-limiting embodiments thereof, reference being made to the accompanying drawings.

DETAILED DESCRIPTION

Figure 1A:
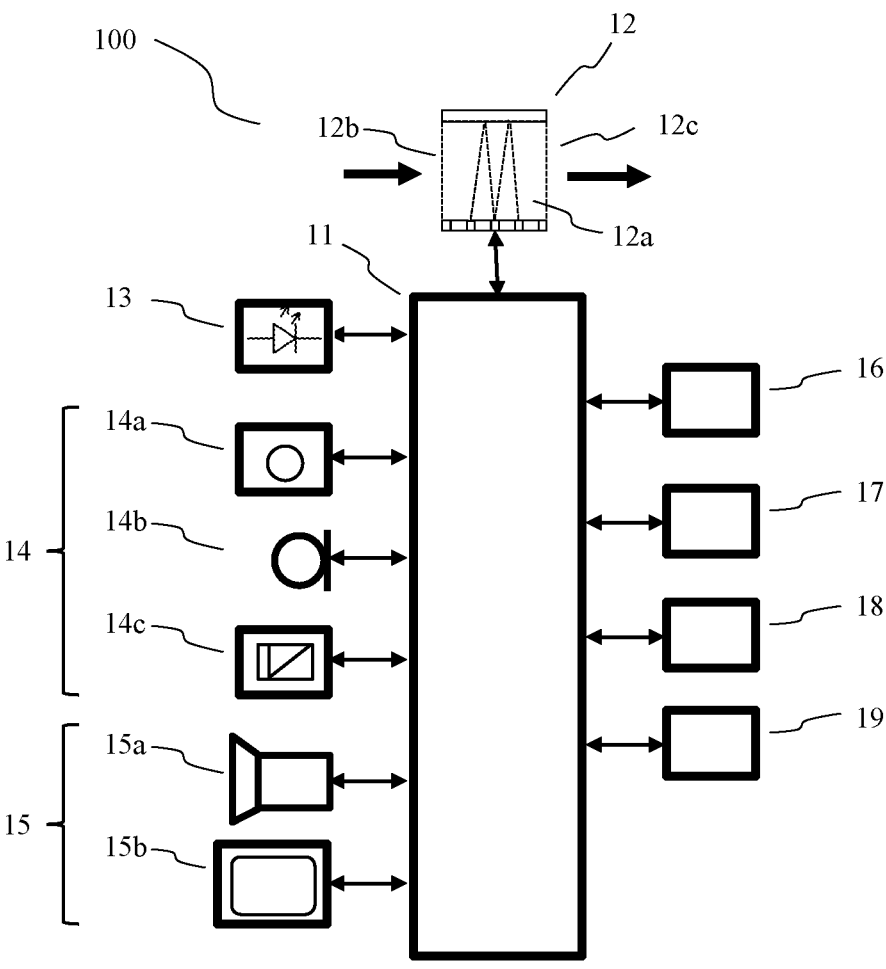
FIG. 1a is a schematic illustration of a breath analysis apparatus according to the present invention.

Terms such as "top", "bottom", upper", lower", "below", "above" etc are used merely with reference to the geometry of the embodiment of the invention shown in the drawings and/or during normal operation of the device/devices and are not intended to limit the invention in any manner.

By classification in the present context is meant judging whether a subject's breath concentration of an intoxicating substance, e g ethyl alcohol, is above or below (at or below) a predefined limit value.

A tracer is a physiological substance inherently associated with expired breath, e g carbon dioxide or water vapor.

By baseline is meant a signal level corresponding to the concentration of intoxicating substance or tracer to which other instantaneous signal values are referred. An offset error is a deviation from the baseline.

A concentration peak is defined by a maximum in a measured concentration versus time with increasing concentration before the peak maximum and declining thereafter.

In the following the breath analysis system and method for determining and classifying an intoxicating substance concentration will be described primarily as a system mounted in and integrated with a vehicle. This is a typical implementation. However, as realized by the skilled person the system and method may also be implemented in other way, for example but not limited to, stand alone systems utilized at the entrance to a restricted work area, a vehicle fleet yard or the like. Modifications for such implementations are apparent for the skilled person in the light of this description.

The breath analysis system and the method according to the invention will primarily be described as a contactless detection system mounted in a vehicle, which represents an important implementation of the invention. As realized by the skilled person, the teachings are equally relevant for stand-alone systems, for example systems at an entrance to a work area, fleet depot or the like. According to some embodiments described hereinafter the system and the method according to the invention may be a combination of a contactless detection system and an active system utilizing a mouthpiece for sampling a breath sample.

A major concern for gaining a public acceptance for widespread or even mandatory sobriety test in for example vehicles is the time required for performing the test and/or if the test is inconvenient for the driver to perform. It should also be realized that although intoxicated drivers is a huge problem, the majority of drivers are sober and hence the sobriety test performed in vehicles may be expected to not detected any illegal amounts of intoxicating substances the vast majority of testing instances. Estimates by the Swedish transport administration gives that 99.8% of drivers have an alcohol concentration below the legal limit. Although the exact number varies in different countries/regions, it is typically well below 1% of all tests that are expected to result in concentrations above legal limits. A breath analyzing system that is fast and convenient for the clearly sober user complying to given instruction, but which will be more time consuming if early indications indicate the existence of an intoxicating substance and/or obstruction by the user is believed to have a good chance of being accepted. The idea of providing a system that has a compliant detection mode as a normal mode of operation and which is fast and convenient for the majority of users and/or the majority of testing occasions and which, if needed, will shift to a interactive detection mode, is part of the inventive concept of the present invention. The interactive detection mode may be seen as a special mode of operation that requires interaction with the user and more time-consuming measurements/analysis and which is used for only a fraction of all testing instances.

FIG. 1a is a schematic drawing of the functional units of the breath analysis system 100 according to the invention and comprises a breath measurement unit 12 comprising a measuring cell or cavity 12a into which a breath sample is drawn for analyzing its content of tracer and intoxicating substances. The breath measurement unit 12 further comprises an inlet 12b connected to one end of the measuring cell 12a and an outlet 12c connected at the other end. The breath measurement unit 12 is further typically provided with a fan for driving an air flow through the measuring cell as well as a heater or heaters for heating up and controlling the temperature of the incoming air. The breath measurement unit 12 will provide an estimate of one or more intoxicating substances associated with the user. The breath measurement unit 12 may be referred to as a primary sensing unit, as the output from this device is central for the further analysis and represents the measure of which decisions are made. Other primary sensing units may be present in the vehicle for example a biometric detector used to verify the identity of the user. One or more visual attraction elements 13 may be provided in the vicinity of the inlet 12b of the breath measurement unit 12. The visual attraction element 13 is provided to attract the user's attention so that he/she will turn towards the visual attraction elements 13 and hence also towards the inlet 12c of the breath measurement unit 12. According to one embodiment the visual attraction element is an LED that is arranged to light up during breath sampling. Alternatively, the visual attraction element 13 may be an indication or an illustration on an existing display, for example an arrow pointing in the direction of the inlet 12c, the arrow being displayed on the existing display during breath sampling.

The breath analysis system 100 may further be provided with at least one secondary sensing unit 14. The secondary sensing unit 14 is arranged to provide other information about the user than the primary sensing unit. Examples of secondary sensing units 14 includes, but are not limited to, a camera 14a in combination with image analysis functionality, a microphone 14b combined with voice recognition functionality, an IR sensor 14c and seat occupation sensors (not shown). The secondary sensing units 14 may be utilized, singularly or in combination to give information on how the user complies with instructions given by the breath analyzing system and also to provide other information that may be useful in the analysis, such as the presence of passengers in the vehicle compartment and their positions.

The breath analysis system 100 is further be provided with at least one interaction unit 15 that is used by the system to convey instructions to the user and may also be arranged to receive responses from the user. Examples of interaction units 15 includes but is not limited to a loudspeaker 15a combined with a voice generation functionality, a display 15b that may display instructions as text messages, images, video and animations, for example. The display 15b may be a touchscreen that also allows for input from the user. Alternatively, other known types of input units may be provided, for example a unit for voice recognition.

The measurement unit 12, the secondary sensing units 14 and the interaction units 15 are in connection with a central processing unit (CPU) 11 which controls the connected devices and receives and process input signals or data from the devices. The breath analysis system 100 may further comprise a wired or wireless communication unit 16 for communication with external entities or with other systems of the vehicle. A long-time memory to serve as a digital library 17 may be provided in connection with the CPU 11 and in which various messages, images or videos are stored to be selected by the CPU 11 to provide different instructions to the user. A program memory 18 is typically included to store the operating sequences of the system. As appreciated by the skilled person means for storage of data, parameters and instructions may be provided in many different ways and the utilization of a digital library 17 in combination with a program memory 18 should be seen as a non-limiting example of a suitable memory configuration. A power supply unit 19 is provided to provide all the units/devices of the system with electric power. Alternatively, the units/devices of the system are powered by a common power supply system of the vehicle.

As realized by the skilled person many of the described units and devices of the breath analysis system 100 are already present in the infotainment system of a modern vehicle. Examples includes loudspeakers in an audio system, microphone(s), means for voice recognition/generation and various displays. An obvious design choice is therefore to "reuse" as much as possible of existing equipment rather than duplicating certain devices. According to one embodiment the breath analysis system 100 is integrated with an infotainment system of a vehicle and at least the CPU, the power supply and the audio system are parts used both by the infotainment system and the breath analysis system 100. Some of the units described above are not necessarily discrete units, for example the voice recognition unit, which typically is a function or application running in the CPU or another processing unit. The skilled person will recognize that the units and functionalities described above may be implemented in different ways and that the choice of a dedicated hardware or a multipurpose hardware with different functionality provided by software or firmware will be made in light of the teaching of the present invention and the constraints and possibilities afforded by the particular implementation. Therefore, the design of the system may be fairly different in for example a stand-alone system breath analyzing system providing all of the above functionality "by itself" compared to a vehicle mounted system having a lot of audiovisual communication facilities already present in the vehicle.

Figure 1B:
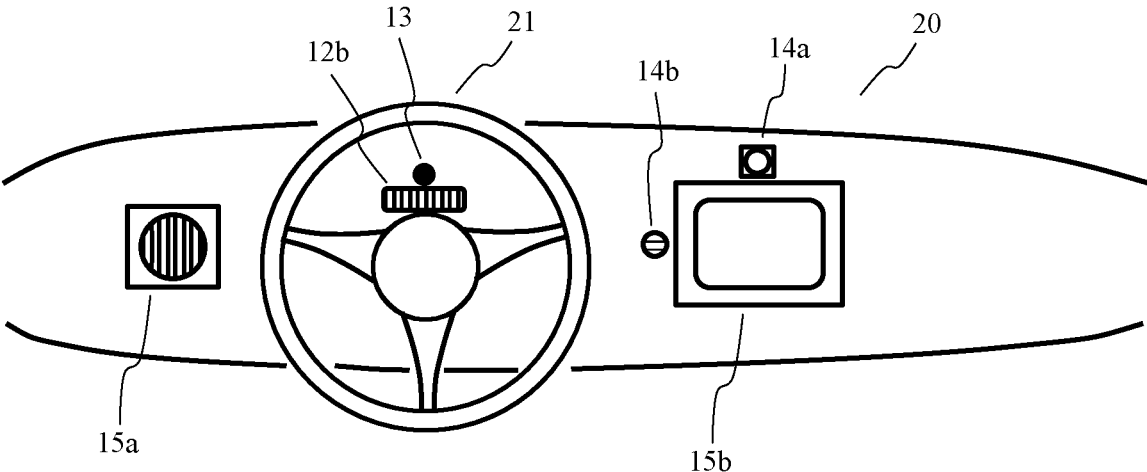
FIG. 1b is a schematic illustration of the system according to the present invention implemented in a dashboard of a vehicle.

An exemplary implementation of the breath analysis system according to the invention is schematically illustrated in FIG. 1*b* showing a dashboard 20 of a vehicle, for example a car. The system is located and integrated with the dashboard 20 and the steering wheel 21. The inlet 12*b* of the breath measurement unit 12 is provided close to the center of the steering wheel 21 and in close vicinity to the inlet 12*b* is a light source located serving as a visual attraction element 13. Secondary sensing units 14 are provided on the dashboard 20 in form of a camera 14*a* and a microphone 14*b* and adapted to monitor of signals related to the driver behavior. Interaction units 15, including a loudspeaker 15*a* and a display 15*b*, for example a touch screen, is also provided on the dashboard 20.

Figure 2:
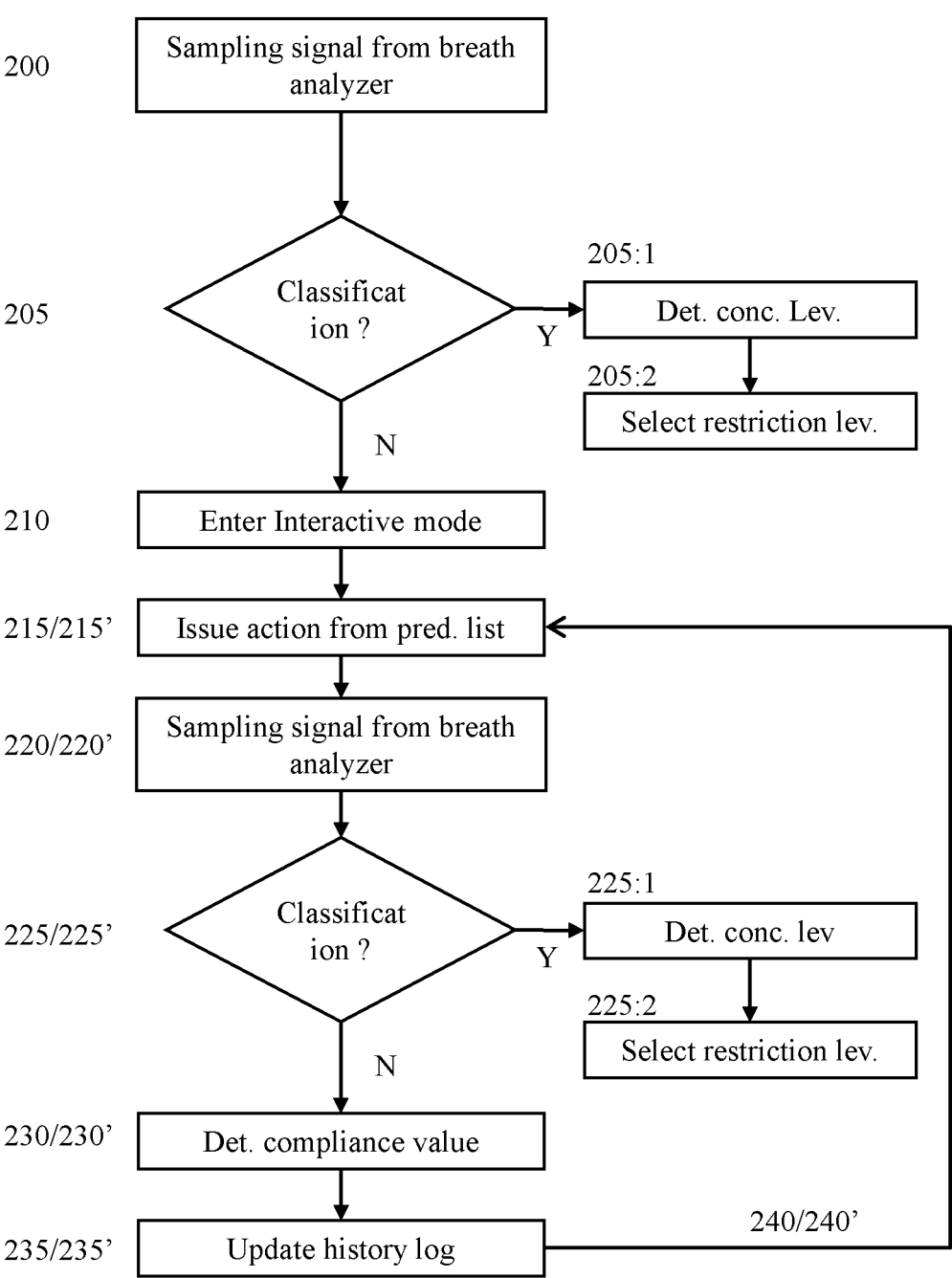
FIG. 2 is a flowchart of the method according to the present invention.

The method according to the invention for determining restriction levels for a user performing a specified task, typically a driver about to start and drive a vehicle is illustrated in the flowchart of FIG. 2. The breath analysis system 100 described with reference to FIG. 1*a-b* is arranged to perform the steps of the method. The method comprises two distinct modes of operation; a compliant mode and an interactive mode. The compliant mode is designed to be fast and not require any specific actions from the driver, more than typically sitting in the driver's seat and breathing normally, which represent a basic instruction that all drivers should have been made aware of. If the driver is sober and compliant to this basic instruction the breath analysis may be performed within less than 10 s, preferably within 5 s. Hence, the method of the invention should be in the compliant mode of operation for the majority of testing occasions, as discussed above. The interactive mode of operation will be entered only if needed, i.e. if the breath analysis could not be correctly performed in the compliant mode. The reason being for example:

the concentration of the intoxicating substance in the exhaled breath appears to be close to the allowed limit but an estimated uncertainty in the measurement is too large to conclusively classify the driver, the breath analysis could not be performed due to the driver is obstructing the procedure, the breath analysis could not be performed due to malfunction of the measurement equipment, the breath analysis could not be performed due to disturbances in the vehicle compartment, for example passengers with alcohol containing breath, open windows on a windy day and presence of substances that disturbs the breath analysis.

any ambiguity of available data, which could include both breath analysis data and input from the secondary sensing units 14.

The interactive mode may take considerably longer time than the compliant mode. However, part of the method according to the invention is the possibility to stepwise increase requirements of interactive response from the user and hence, the time needed for performing the classification is also stepwise increased. For example, a first failure to perform the classification may typically result, as a first attempt, in an issued action to the user that is relatively quick to perform.

One part of the interactive mode of operation is to establish an action compliance value which must exceed minimum requirements to enable classification of the user's driving capability in terms of restriction levels. A session history log including recorded data during the session is used as a tool for determining updated versions of the action compliance value. The session history log comprises information on the issued selected actions in the present interactive mode session and the corresponding result of the issued selected actions, and the action compliance value is a value determined from the result of the issued selected actions At the starting point of the interactive mode of operation, the action compliance value is quantified to be below the required threshold to allow classification into restriction level. By providing more detailed instructions and requests, and obtaining more data, the action compliance value is updated based on these data. By the computed updated action compliance value, the user's driving capability in terms of an applicable restriction level can be determined. The contents of the session history log is obtained using recorded data from sensor signals during the session by which the action compliance value is being computed.

The method according to the invention utilizes two sets of parameters and/or instructions, wherein the content of the sets has been provided and stored previously:

set of restriction levels containing restriction levels, for example "drive without restriction", "drive with warning issued", "limited drivability", and "ignition locking". A certain restriction level may be selected based on the measured breath concentration of an intoxicating substance of the user, wherein a first concentration interval corresponds to a first restriction level, a second concentration interval corresponds to a second restriction level, etc.

The concentration intervals may correspond to legal levels of one or more intoxicating substances and may additionally take into account physiological aspects such as the subject is in the absorption or elimination phase of the substance concentration kinetics. In addition, in the interactive mode, non-compliance to an issued instruction may affect the selection of the restriction level so that even if the classification could not be performed, a restriction level limiting the drivability is selected. Also, if the intoxicating substance breath concentration is measured to be within the first interval, for example, a higher restriction level could be selected if non-compliance is determined, for example based on input from the secondary sensing units 14.

set of predetermined actions for example comprising the actions:

activate the visual attraction element, issue instruction: "face detector"; "lean forward, exhale towards inlet 12*b* face detector"

issue warning: "still missing data, if not remedied driving will be restricted or stopped"

The content may vary depending on the present implementation of the system and method as an adaptation to variations in availability of for example secondary sensing units 14 and/or type of interaction units 15. Thereby the method according to the invention is adaptable to different hardware configurations by typically only having to update the content of the sets. Further, how the actions will be carried out in detail will depend on hardware configurations and the equipment in the vehicle. For example, ignition locking may be provided as a separate existing function in the vehicle, but if not, an equivalent locking effect may be provided by other means.

The compliant mode of operation according to the method of the invention comprises the steps of

200: sampling signals representing the local concentration of an intoxicating substance, analyzing the sampling result and determining from the analyzed results if the breath concentration of an intoxicating substance of the user may be classified within required levels of accuracy and precision;

205: if classification is determined to be possible to perform:

205:1: determining intoxicating substance breath concentration, and

205:2: comparing the intoxicating substance breath concentration with a set of predetermined concentration intervals to select a restriction level from a predetermined set of restriction levels, wherein each predetermined concentration interval corresponds to a predetermined restriction level;

210: if classification is determined to not be possible to perform the method enters into the interactive mode of operation.

The interactive mode of operation comprises the steps of:

215: issue a selected action to the user from a set of predetermined actions, the selection of an instruction based on a session history log and an action compliance value;

220: sampling signals representing the local concentration of an intoxicating substance and analyzing the sampling result and determining from the analyzed results if the breath concentration of an intoxicating substance of the user may be classified within required levels of accuracy and precision;

225: if classification is determined to be possible:

225:1 determining the intoxicating substance breath concentration, and

225:2: comparing the intoxicating substance breath concentration with a set of predetermined concentration intervals to select a restriction level from a predetermined set of restriction levels, wherein each predetermined concentration interval corresponds to a predetermined restriction level; and if classification is determined to not be possible:

230: determining an action compliance value based on an analysis of how well the user has complied to the issued selected action;

235: updating the session history log, the session history log comprising information of which action of the set of predetermined actions that have been issued;

240: repeating the steps of the interactive mode (215-235) until a restriction level is established or a predetermined maximum time period is reached.

Determining if classification is possible, step 205 and 225, should be interpreted as being possible to measure the concentration of the intoxicating substance in the exhaled breath of the user with an acceptable accuracy and precision and to classify if the concentration is above or below a predetermined level, typically a legal level or within a predetermined interval. An acceptable accuracy/precision may typically and preferably be determined by statistical analysis of the sampled data, typically also combined with knowledge of known error levels and predictable fluctuations in the breath analysis system, for example temperature dependencies. Due to the importance of the classification being correct it is of high importance that the complete measuring process is performed in a manner so that the measure of the concentration has a high degree of certainty. It may also be eligible to include a "safety margin" in using the measured result for determination of a restriction level, for example to take into account the fact that determination of a certain concentration at one point in time may after some time be invalid depending on whether the subject is in the absorption or elimination phase of the substance concentration kinetics. This aspect is particularly important where the legal limit is low, for example in Sweden. Typical duration of the absorption phase is 30 minutes, in a wide range of alcohol concentrations. The elimination is typically linear with time but may vary considerably from one individual to another. Typically, one centiliter of pure alcohol is metabolized in one hour.

The skilled person is, given that a predetermined level of accuracy and precision is required, capable of implementing a suitable measurement system and measuring scheme. The co-pending application SE 2050105-2 by the same applicant as the present invention provides a particularly time effective system and method to perform accurate and precis measurements and classifications.

According to one embodiment the intoxicating substance is alcohol and the measurement performed by the breath analysis system is a BrAC measurement (BrAC—breath alcohol concentration). A preferred method is a tracer gas measurement based system as described in for example U.S. Pat. Nos. 7,919,754 and 9,746,454.

According to one embodiment the set of restriction levels comprises a plurality of actions or settings representing increasing limitations to drivability of the vehicle. The set of restriction levels may include: issue a warning to the user, set the vehicle in a limited drivability mode, and ignition locking. One restriction level should typically represent completely unrestricted use of the vehicle, to be used in the case that the method has entered into the interactive mode of operation, and the further steps gives the result that user complies to the given instructions and any concentration of the intoxicating substance is below the lowest legal limit. According to one embodiment the set of restriction levels comprises: No restriction of use of the vehicle and at least one of the following: Issue a warning to the user, Set the vehicle in a limited drivability mode, and Ignition locking. Depending on the nature of the restriction level determined by the method and breath analysis system 100, the result may be communicated to other systems/functions of the vehicle, for example an Ignition lock. The result may also be communicated to external entities, for example to a fleet management system.

According to one embodiment the set of predetermined actions comprises a plurality of actions that may be grouped according to:

attention actions, for example activating the visual attraction element 13.

instructive actions, for example issue an instruction "please face the detector" using the interaction unit 15 requests for action, for example urging the driver to lean forward to the inlet 12*b* combined with a message that states that if the user does not comply, restrictions in the driving ability may follow.

warning actions, for example issue a warning "Your ability to drive has not been verified due to missing data" using the interaction unit 15.

According to one embodiment determining the action compliance value comprises evaluating the sampling results and wherein an improved classification support results in an increased action compliance value even if the sampling result would still be inadequate for final classification. Determining the action compliance value may comprise evaluating secondary input data. Secondary input data is typically data received from one or more of the secondary sensing unit 14. The secondary input data may comprise video or images, signals from IR sensors (for detecting the presence of the user or passengers) and seat occupation sensors. The user behavior is analyzed and classified from video and/or image analysis or the other signals, or from a combination of them. The analysis may range from establishing the presence of a user to advanced image processing recognizing that a number of persons are present in the vehicle and their activity.

According to one embodiment a further step is introduced to be taken upon a selected action, typically a warning action being issued, the further step comprising the user confirming that he/she has comprehended the warning and the system receiving and preferably storing such confirmation. In the same manner the user may in a step, to be taken after a restriction has been issued, be asked to confirm acceptance of the restriction. Confirmations may be inputted to the system via the interaction unit 15.

According to one embodiment the action compliance value determined in step 230, is based on an analysis if the measurement of the intoxicating substance has improved the possibility to classify to the predetermined level of certainty.

According to one embodiment the interactive mode of operation comprises utilizing at least one secondary sensing unit 14. The secondary sensing unit 14 provides a user compliance input that is used in the step 230 of determining an action compliance value. The action compliance value may be based on both the further user compliance input and the change (improvement anticipated) of measurement result of the intoxicating substance. The user compliance input provided by the secondary sensing unit 14 may for example be images provided by the camera 14*a* in combination with image analysis functionality, which supposedly indicates if the user has followed the instruction to, for example, face the detector or not. The action compliance value is preferably parameterized to a set of integer values. One example is to have three values, wherein the value 1 corresponds to the user not following the instructions of the selected action, value 2 to partly following the instructions and value 3 fully following the instructions. The values may be determined from image or video analysis, wherein, for example upon the instruction "lean forward to the inlet", value 1 is the user deliberately directing his/hers breath away from the sensor, value 2 is directing the breath towards the inlet, and value three is the user actually leaning close to the inlet. Such image/video analysis is possible for the skilled person to implement with existing methods. The analysis is not limited to the use of only one secondary sensing unit 14. For example, input from a camera 14*a* in combination with image analysis functionality, a microphone 14*b* combined with voice recognition functionality, an IR sensor 14*c* and seat occupation sensors in various combination may advantageously be used in order to analyze the users behavior after an action has been issued and provide the action compliance value. It should also be understood that typically the action compliance value is dependent on the instruction issued and also on the session history log.

The session history log comprises a listing of issued selected actions and corresponding action compliance values and may typically be stored in program memory 18. According to one embodiment the session history log is renewed for each session, a session for example being one driving session or one entering to a restricted area. According to one embodiment the history session log is maintained for a predetermined time period, for example in the order of 30 min. This is to prevent that a user would abort the starting up procedure for the vehicle in an attempt to manipulate the system. Such function is preferably combined with an identification mechanism of the user, so that the history session log is reset if user changes. When the subject's identity is known from any of the available data sources, the compliance value may be personalized by comparing the actual compliance with normal behavior of that particular subject, as available from previous session history logs According to one embodiment of the invention at least one secondary sensing unit 14 is activated in the compliant mode, and if the information retrievable from secondary sensing unit 14 indicates tampering with the breath analysis, the compliant mode is aborted and the method goes directly to the interactive mode.

According to one embodiment of the invention utilizing the breath analysis system 100 described with reference to FIGS. 1*a* and 1*b*, the interactive mode of operation comprises the steps of:

215': issue a selected action to the user from a set of predetermined actions, the selection of an instruction based on a session history log and an action compliance value, wherein the selected action is issued via the visual attraction element 13 and/or the interaction unit 15;

220': sampling signals from a breath measurement unit 12 representing the local concentration of an intoxicating substance and analyzing the sampling result, analyzing the sampling result and determining from the analyzed results if the breath concentration of an intoxicating substance of the user may be classified within required levels of accuracy and precision;

225': if classification is determined to be possible to perform with the required levels of accuracy and precision:

225:1': determining the intoxicating substance breath concentration, and

225:2': comparing the intoxicating substance breath concentration with a set of predetermined concentration intervals to select a restriction level from a predetermined set of restriction levels, wherein each predetermined concentration interval corresponds to a predetermined restriction level; and if classification is determined to not be possible:

230': determining an action compliance value based on an analysis of how well the user has complied to the issued selected action, using input from at least one secondary sensing unit 14, the secondary sensing unit providing other information about the user than the breath measurement unit 12;

235': updating the session history log, the session history log comprising information of which action of the set of predetermined actions that have been issued;

240: repeating the steps of the interactive mode (215-235) until a restriction level is established or a predetermined maximum time period is reached.

According to one embodiment the selected action issued in step 215' comprises the breath analyzing system 100 using one or a combination of the interaction units 15: a loudspeaker 15a, typically and preferably combined with a voice generation functionality, a display 15b that may display instructions as text messages, images, video and animations, for example. The display 15b may be a touchscreen that also allows for input from the user.

According to one embodiment the determining an action compliance value selected action is issued in step 230' comprises one or a combination of the secondary sensing units 14: a camera 14a in combination with image analysis functionality, a microphone 14b combined with voice recognition functionality, an IR sensor 14c and seat occupation sensors.

According to one embodiment of the invention the step of selecting a restriction level from a predetermined set of restriction levels, steps 205:2: 225:2/225:2' further comprises informing the user about the restriction level using one or a combination of the interaction units 15.

The use of the system and the method according to the invention may be illustrated from a time-consumption view. The compliant detection mode should be completed within 5 seconds. The decision process in the interactive detection mode which is based on breath analysis sensor data and the driver's response/compliance may include the following four major phases (and their time windows from start):

Attention (0-5 seconds)
Instruction (5-10 seconds)
Request for action (10-20 seconds)
Warning (20-30 seconds)

Figure 3:
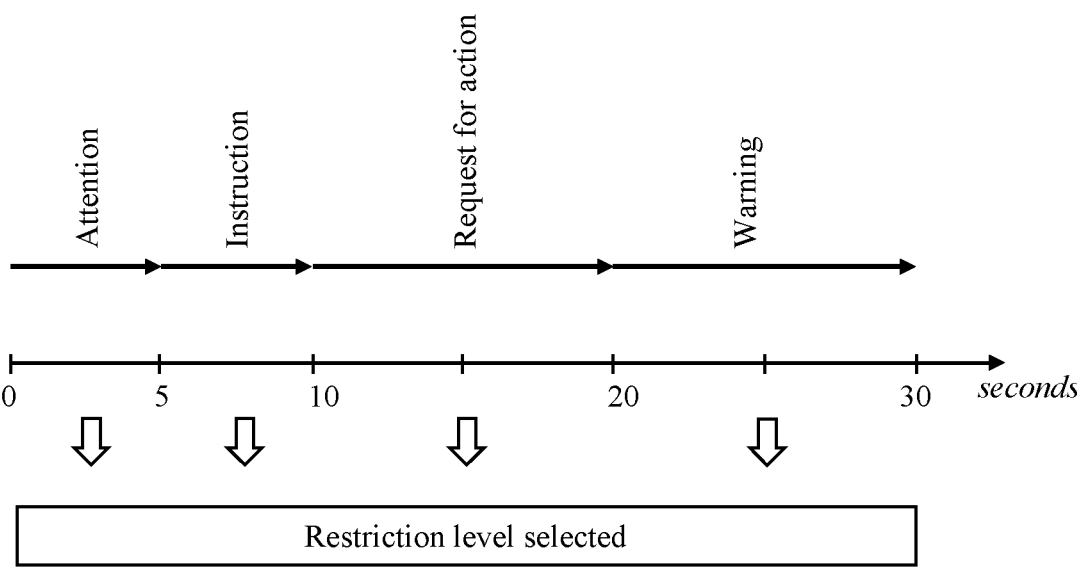
FIG. 3 is a graph illustrating how the method and system according to the invention provides analysis results with regards to time from starting the process.

The division levels into four major phases and the timings are illustrated in FIG. 3. An experienced sober driver will normally be approved within 3-5 seconds and allowed to drive without restrictions. If data is missing the driver will receive detailed instructions on how to provide an approvable breath sample before drivability of the vehicle will be enabled. If data for breath analysis is still missing after 10 seconds, a request for action will be issued with repeated and more detailed instructions. If data is still missing after 20 seconds a warning will be issued. The final drivability decision, the restriction level, will in this scenario be issued after 30 seconds.

The embodiments described above are to be understood as illustrative examples of the system and method of the present invention. It will be understood that those skilled in the art that various modifications, combinations and changes may be made to the embodiments. In particular, different part solutions in the different embodiments can be combined in other configurations, where technically possible.

The invention claimed is:

1. A method for operating a breath analysis system (100) to determine restriction levels for a user performing a specified task based on a concentration of an intoxicating substance in the exhaled breath of the user and an analysis of the behavior of the user, the method comprising a compliant mode of operation and an interactive mode of operation, the method utilizing a predetermined set of restriction levels and a predetermined set of actions, wherein the compliant mode comprising the steps of:

(200) sampling signals representing the local concentration of an intoxicating substance, analyzing the sampling result and determining from the analyzed results if the breath concentration of an intoxicating substance of the user may be classified within required levels of accuracy and precision;

(205) if classification is determined to be possible to perform:

(205:1) determining intoxicating substance breath concentration, and (205:2) comparing the intoxicating substance breath concentration with a set of predetermined concentration intervals to select a restriction level from a predetermined set of restriction levels, wherein each predetermined concentration interval corresponds to a predetermined restriction level;

(210) if classification is determined to not be possible to perform the method enters into the interactive mode of operation, the interactive mode of operation comprising the steps of:

(215; 215') issuing a selected action to the user from a set of predetermined actions, the selection of an instruction based on a session history log and an action compliance value, wherein the session history log comprises information on the issued selected actions in the present interactive mode session and the corresponding result of the issued selected actions, and the action compliance value is a value determined from the result of the issued selected actions;

(220; 220') sampling signals representing the local concentration of an intoxicating substance and analyzing the sampling result and determining from the analyzed results if the breath concentration of an intoxicating substance of the user may be classified within required levels of accuracy and precision;

(225; 225') if classification is determined to be possible:

(225:1; 225:1') determining the intoxicating substance breath concentration, and (225:2; 225:2') comparing the intoxicating substance breath concentration with a set of predetermined concentration intervals to select a restriction level from a predetermined set of restriction levels, wherein each predetermined concentration interval corresponds to a predetermined restriction level; and if classification is determined to not be possible:

(230; 230') determining an action compliance value based on an analysis of how well the user has complied to the issued selected action;

(235; 235') updating the session history log, the session history log at least comprising information of which action of the set of predetermined actions that have been issued;

(240; 240') repeating the steps of the interactive mode (215-235) until a restriction level is established.

2. The method according to claim 1, wherein the set of restriction levels comprises a plurality of restriction levels representing increasing limitations to drivability of the vehicle.

3. The method according to claim 2, wherein the set of restriction levels comprise one or more of the restriction levels corresponding to settings of the vehicle: drive without restriction, drive with warning issued, limited drivability, and ignition locking.

4. The method according to claim 1, wherein the set of predetermined actions comprises at least one of the subsets of: attention actions, instructive actions, requests for action, and warning actions.

5. The method according to claim 4, wherein an attention action comprises activating a visual attraction element (13).

6. The method according to claim 4, wherein an interaction unit (15) is used by the breath analysis system (100) to communicate the action to the user.

7. The method according to claim 1, comprising a further step to be taken upon a selected action being issued, the further step comprising receiving a confirmation from the user confirming comprehension and acceptance of the selected action.

8. The method according to claim 1, wherein the action compliance value determined in step (230; 230'), is based on an analysis if the measurement of the intoxicating substance has improved the possibility to classify within required levels of accuracy and precision.

9. The method according to claim 1, wherein the action compliance value determined in step (230; 230'), is at least partly based on input provided by a secondary sensing unit 13.

10. The method according to claim 1, wherein the interactive mode of operation comprises the steps of:

(215') issuing a selected action to the user from a set of predetermined actions, the selection of an instruction based on a session history log and an action compliance value, wherein the selected action is issued via the visual attraction element (13) and/or the interaction unit (15);

(220') sampling signals from a breath measurement unit (12) representing the local concentration of an intoxicating substance and analyzing the sampling result, analyzing the sampling result and determining from the analyzed results if the breath concentration of an intoxicating substance of the user may be classified within required levels of accuracy and precision;

(225') if classification is determined to be possible to perform within the required levels of accuracy and precision:

(225:1') determining the intoxicating substance breath concentration, and (225:2') comparing the intoxicating substance breath concentration with a set of predetermined concentration intervals to select a restriction level from a predetermined set of restriction levels, wherein each predetermined concentration interval corresponds to a predetermined restriction level; and if classification is determined to not be possible:

(230') determining an action compliance value based on an analysis of how well the user has complied to the issued selected action, using input from at least one secondary sensing unit (14), the secondary sensing unit providing other information about the user than the breath measurement unit (12);

(235') updating the session history log, the session history log comprising information of which action of the set of predetermined actions that have been issued;

(240') repeating the steps of the interactive mode (215-235) until a restriction level is established.

11. The method according to claim 10, wherein the step of issuing the selected action (215') comprises the breath analyzing system (100) using one or a combination of the interaction units (15): a loudspeaker (15a), and a display (15b).

12. The method according to claim 10, wherein determining an action compliance value (230') after the selected action is issued comprises using one or a combination of the secondary sensing units (14): a camera (14a) combined with image analysis functionality, a microphone (14b) combined with voice recognition functionality, an IR sensor (14c) and seat occupation sensors.

13. A breath analysis system (100) comprising a breath measurement unit (12) at least one visual attraction elements (13), at least one secondary sensing unit (14), at least one interaction unit (15), and a CPU (11), wherein the breath analysis system (100) is configured to provide a compliant mode comprising the steps of:

(200) sampling signals from the breath measurement unit (12) representing the local concentration of an intoxicating substance, analyzing the sampling result and determining from the analyzed results if the breath concentration of an intoxicating substance of the user may be classified within required levels of accuracy and precision;

(205) if classification is determined to be possible to perform:

(205:1) determining intoxicating substance breath concentration, and (205:2) comparing the intoxicating substance breath concentration with a set of predetermined concentration intervals to select a restriction level from a predetermined set of restriction levels, wherein each predetermined concentration interval corresponds to a predetermined restriction level, and (210) if classification is determined to not be possible to perform the provide an interactive mode of operation, the interactive mode of operation comprising the steps of:

(215') issuing a selected action to the user from a set of predetermined actions, the selection of an instruction based on a session history log and an action compliance value, wherein the session history log comprises information on the issued selected actions in the present interactive mode session and the corresponding result of the issued selected actions, and wherein the selected action is issued via the visual attraction element (13) and/or the interaction unit (15);

(220') sampling signals from a breath measurement unit (12) representing the local concentration of an intoxicating substance and analyzing the sampling result, analyzing the sampling result and determining from the analyzed results if the breath concentration of an intoxicating substance of the user may be classified within required levels of accuracy and precision;

(225') if classification is determined to be possible to perform within the required levels of accuracy and precision:

(225:1') determining the intoxicating substance breath concentration, and (225:2') comparing the intoxicating substance breath concentration with a set of predetermined concentration intervals to select a restriction level from a predetermined set of restriction levels, wherein each predetermined concentration interval corresponds to a predetermined restriction level; and if classification is determined to not be possible:

(230') determining an action compliance value based on an analysis of how well the user has complied to the issued selected action, using input from at least one secondary sensing unit (14), the secondary sensing unit providing other information about the user than the breath measurement unit (12);

(235') updating the session history log, the session history log comprising information of which action of the set of predetermined actions that have been issued;

(240') repeating the steps of the interactive mode (215-235) until a restriction level is established.

14. The method according to claim 1, wherein the repetition of the steps of the interactive mode (215-235) is terminated if a predetermined maximum time period is reached.

15. The system according to claim 13, wherein the secondary sensing unit 14 is one of or a combination of: a camera 14 *a*, a microphone 14 *b*, an IR sensor 14 *c* and seat occupation sensor.

\* \* \* \* \*